United States Patent [19]

Phillips et al.

[11] Patent Number: 5,158,760
[45] Date of Patent: Oct. 27, 1992

[54] $^{99m}$ TC LABELED LIPOSOMES

[75] Inventors: William T. Phillips; Robert W. Klipper, both of San Antonio, Tex.; James H. Timmons, Tacoma, Wash.; Alan S. Rudolph, Bowie, Md.

[73] Assignees: Board of Regents, The University of Texas System, Austin, Tex.; The United States of America as represented by the Secretary of the Navy, Washington, D.C.

[21] Appl. No.: 530,847

[22] Filed: May 30, 1990

[51] Int. Cl.$^5$ ............ A61K 43/00; A61K 49/02; A61K 9/127; A61K 9/133
[52] U.S. Cl. .................. 424/1.1; 424/450; 436/829; 534/14
[58] Field of Search .............. 424/1.1, 450; 534/14; 436/829

[56]  References Cited

U.S. PATENT DOCUMENTS

| | | | |
|---|---|---|---|
| 4,335,095 | 6/1982 | Kelly | 424/1.1 |
| 4,452,774 | 6/1984 | Jones et al. | 424/1.1 |
| 4,466,951 | 8/1984 | Pittman | 424/1.1 |
| 4,497,791 | 2/1985 | Gamble et al. | 424/1.1 |
| 4,615,876 | 10/1986 | Troutner et al. | 424/1.1 |
| 4,705,678 | 11/1987 | Goedemans | 424/1.1 |
| 4,707,544 | 11/1987 | Jones et al. | 534/14 |
| 4,735,793 | 4/1988 | Jones et al. | 424/1.1 |
| 4,789,736 | 12/1988 | Canning et al. | 534/14 |
| 4,818,813 | 4/1989 | Nowotnik et al. | 424/1.1 X |
| 4,826,961 | 4/1989 | Jones et al. | 534/14 |
| 4,911,929 | 3/1990 | Farmer et al. | 424/450 |
| 4,925,650 | 11/1988 | Nosco et al. | 424/1.1 |
| 4,935,223 | 6/1990 | Phillips | 424/1.1 |
| 4,938,947 | 7/1990 | Nicolau et al. | 424/1.1 |

OTHER PUBLICATIONS

Article by Lang, Letters to the Editor, J. Nucl. Med., 31(6):1115 (1990).
Article by Ballinger, Letters to the Editor, J. Nucl. Med., 31(6):1116 (1990).
Article by Ballinger et al., "Technetium-99m HM-PAO Stereoisomers: Differences in Interaction with Glutathione", J. Nucl. Med., 29(12):1998-2000 (1988).
Atsushi Takeda et al. "Intensification of Tumor Affinity of $^{99m}$TC-DL-Homocysteine by Cooperative Use of SH-containing Compounds", Nucl. Med. Biol., vol. 16, No. 16, pp. 581-585, 1989.
Claire De Labriolle-Vaylet et al., "Morphological and Functional Status of Leukocytes Labelled with $^{99m}$ Technetium HMPAO", Radiolabelled Cellular Blood Elements, pp. 119-129.
Laurence Guilloteau et al., "Recruitment of $^{99m}$-Technetium- or 111-Indium-Labelled Polymorphonuclear Leucocytes in Experimentally Induced Polygranulomas in Lambs", J. of Leukocyte Bio., vol. 48, pp. 343-352, (1990).
Dialog Search Report.
Karl J. Hwang, "Liposome Pharmacokinetics," In: Liposomes from Biophysics to Therapeutics (M. J. Ostro, Ed.), pp. 109-156 (Marcel Dekker, Inc.) New York 1987.
Caride and Sostman, "Methodological Considerations for the Use of Liposomes in Diagnostic Imaging," Liposome Technology, vol. II:107-124 (1984).

(List continued on next page.)

Primary Examiner—Richard D. Lovering
Assistant Examiner—John M. Covert
Attorney, Agent, or Firm—Arnold, White & Durkee

[57]  ABSTRACT

The invention relates to a $^{99m}$Tc-labeled liposome encapsulated protein and to a highly efficient method of radiolabeling liposome encapsulated protein. In particular, a $^{99m}$Tc carrier is used to label preformed liposome-encapsulated hemoglobin. The liposome-encapsulated $^{99m}$Tc labeled hemoglobin is highly stable in vitro and in vivo and is suitable for a variety of clinical uses, including biodistribution imaging studies. The invention also relates to a method of using technetium-$^{99m}$ labeled liposome encapsulated hemoglobin to label neutrophils. A kit method which could be used for the convenient preparation of $^{99m}$Tc-labeled liposome encapsulated hemoglobin for clinical use is also disclosed.

15 Claims, 5 Drawing Sheets

99m TC LABELED LIPOSOMES

The United States Government may have a paid-up license in this invention and the right in limited circumstances to require the patent owner to license others on reasonable terms as provided for by the terms of Grant No. N 00014-89-K-0077 awarded by the Office of Naval Research.

BACKGROUND OF THE INVENTION

1. Field of the Invention

The invention relates to a rapid and highly efficient method of labeling liposome encapsulated protein. In particular, the method relates to the radionuclide labeling of preformed liposomes containing a protein to which the radionuclide selectively binds.

Table 1 is a list of abbreviations used.

TABLE 1

| | |
|---|---|
| cpm | counts per minute |
| DTPA | diethylenetriaminepenta-acetic acid |
| GBq | gigabequerels |
| HMPAO | hexamethylenepropylene amine oxime |
| LEH | liposome encapsulated hemoglobin |
| PBS | phosphate buffered saline |
| PYP | pyrophosphate |
| Tc | Technetium |
| LUV | large unilamellar vesicles |

2. Description of Related Art

Liposomes are of considerable interest because of their value as carriers for diagnostic agents, particularly radiopharmaceuticals for tracer and imaging studies. Successful biodistribution studies, for example, require the entrapment of high specific activities of a radiolabel in the aqueous compartment of the liposome. Unfortunately, the entrapment of water soluble radionuclides within the liposome is relatively inefficient. Another major problem in using liposomes is their leakiness, resulting in limited usefulness for many applications (Hwang, K. J., in Liposomes from Biophysics to Therapeutics, M. J. Ostru, Ed., Marcel Dekker, New York, 1987).

Radioactive markers have been widely used as a noninvasive method for studying the distribution of drugs in vivo. The use of gamma emitting radioisotopes is particularly advantageous because, unlike beta-emitters, they can easily be counted in a scintillation well counter and do not require tissue homogenization prior to counting. In addition, gamma-emitters can be imaged with nuclear gamma cameras. With this type of imaging, the dynamic biodistribution can be followed noninvasively using consecutive one minute computer acquired scintigraphic images which are analyzed to calculate organ biodistribution curves.

The most common radiolabel used in diagnostic radiopharmaceuticals today is $^{99m}$Tc. This radionuclide is produced from the beta decay of molybdenum$^{99}$ and has a half-life of 6 hours. It is widely available from a generator system at low cost and its relatively short half-life provides for safer and more convenient handling than other available radionuclides. Its gamma emission is in the range of 140 Kev which is an ideal range for producing high resolution images (Caride, V. J. and Sostman, H. D. in Liposome Technology, Vol. II, G. Gregoriadis, Ed., CRC Press, Boca Raton, 1984). Heptavalent $^{99m}$TcO$_4^-$ is produced from the generator and since it is relatively unreactive, must be reduced to a lower oxidation state before use as a radiopharmaceutical. Stannous chloride is the most commonly used reducing agent (Barratt, G. M., Tuzel, N. S. and Ryman, B. E. in Liposome Technology, Vol. II, G. Gregoriadis, Ed., CRC Press, Boca Raton, 1984).

Radiolabeled complexes have been employed as a means for labeling liposomes. Isonitrile radionuclide complexes of Tc and other gamma-emitters appear to have use for labeling vesicles with lipid membranes, including red blood cells (U.S. Pat. No. 4,452,774, Jones et al., Jun. 5, 1984). Propyleneamine oxime complexes with $^{99m}$Tc are stable neutral lipophilic complexes which have been approved for radioimaging in vivo as an adjunct in the detection of altered regional cerebral perfusion (Ceretec TM ) These complexes which diffuse across cellular walls have been shown to localize in red blood cells, although radioactivity is readily washed from the cells. (U.S. Pat. No. 4 615 876 Troutner et al. Oct. 7, 1986) Furthermore, the usefulness of these complexes is limited because the complexes are not stable. Ceretec TM , for example, has a useful life of approximately 30 minutes.

A radionuclide of indium has found some use as an imaging agent. Multilamellar lipid vesicles labeled with $^{111}$In using 8-hydroxyquinoline showed a labeling efficiency of 30% (Caride, V. J. and Sostman, H. D. in Liposome Technology, Vol. II, G. Gregoriadis, Ed., CRC Press, Boca Raton, 1984). Higher labeling efficiencies have been shown for loading $^{111}$In into the aqueous compartment of liposomes. Acetylacetone, a water soluble lipophilic chelator, can be complexed with $^{111}$In. This is then mixed with liposome encapsulated nitrilotriacetic acid with subsequent formation of labeled nitrilotriacetic acid. The resulting labeled liposomes are unstable unless excess acetylacetone is removed by an ion exchange process (Beaumier, P. L. and Hwang, K. J., J. Nucl. Med. 23, 810–815 (1982)).

In general, labeling efficiency of 50–70% for $^{99m}$Tc has been reported for multilamellar vesicles and 4–20% for small unilamellar vesicles when using stannous chloride to reduce the pertechnetate. A persistent problem in all these methods is the removal of excess reducing agent as well as elimination of free pertechnetate. Separation can be done by gel filtration or dialysis, but there is often formation of a $^{99m}$Tc-tin chloride colloid which is not readily distinguishable or separable from the liposomes (Barratt, G. M., Tuzel, N. S. and Ryman, B. E. in Liposome Technology, Vol. II, G. Gregoriadis, Ed., CRC Press, Boca Raton, 1984). This confounds the results of biodistribution studies since interpretation may be subject to altered uptake influenced by the labeled colloidal tin.

Attempts at labeling liposomes with imaging radiotracers have produced variable results (Barratt, G. M., Tuzel, N. S. and Ruman, B. E. in Liposome Technology, Vol. II, G. Gregoriadis, Ed., CRC Press, Boca Raton, 1984; Caride, V. J. and Sostman, H. D. in Lipid Technology, Vol. II, G. Gregoriadis, Ed., CRC Press, Boca Raton, 1984; Caride, V. J., Nucl. Med. Biol. 17, 35–39 (1990); Hwang, K. J. in Liposomes from Biophysics to Therapeutics, M. J. Ostro, Ed., Marcel Dekker, Inc., New York, 1987). Many radioisotope labels weakly bind to liposomes resulting in inaccurate biodistribution data. A more efficient imaging label procedure uses $^{111}$indium chloride ($^{111}$InCl) and nitrilotriacetic acid, a metal chelator (Beaumier, P. L. and Hwang, K. J., J. Nucl. Med. 23, 810–815 (1982); Turner, A. F., Prasent, C. A., Proffitt, R. T., Williams, L. E., Winsor, D. W., Werner, J. L., *Radiology* 166, 761–765 (1988); proffitt, R. T., Williams, L. E., Presant, C. A., Tin, G. W., Uliana, J. A., Gamble, R. C. and Baldeschwieler, J. D., *J. Nucl. Med.* 24, 45–51 (1983). The nitrilotriacetic acid is incorporated into the liposome during the manufacturing process. The preformed liposomes are then incubated for 30 minutes with $^{111}$InCl. Although the $^{111}$InCl nitrilotriacetic acid labeling method has proven to be effective and the label tightly attached to the liposome, a heating step (60° C.) is required, which adds to the time and inconvenience involved in the preparation. In a clinical situation convenience and speed are important. A further consideration is the expense of the $^{111}$In radionuclide. The present cost of $^{111}$In is approximately \$135/mCi while cost of $^{99m}$Tc, a superior imaging agent, is \$0.35/mCi. This difference is highly significant in determining cost of imaging procedures to the patient and in a decision by the health provider to offer such services.

Other labeling carriers have been tried. Small amounts of octadecylamine-DTPA (diethylene-triaminepenta-acetic acid) in liposomes have been shown to rapidly label the liposomes with $^{67}$Ga or $^{99m}$Tc by chelation with efficient labeling, but over 30% of the label is lost after a 2 hour incubation in plasma (Hnatowich, D. J., Friedman, B., Clancy, and Novak, M. *J. Nucl. Med.* 22, 810–814 (1981).

The reasons for instability of $^{99m}$Tc labeled liposomes are not well understood, although instability may be related to the liposome surface charge. Recent work has shown that the in vitro methods currently used to assess the stability of labeled liposomes do not predict isotope stability in vivo, and that the nature of the binding between the isotope and the liposome surface is important in regulating in vivo isotope stability (Love, W. G., Amos, N., Williams, B. D., and Kellaway, I. W., *J. Microencapsulation* 6, 103–113 (1989)). The result is that even when labeling methods appeared to be highly efficient, and little instability was demonstrated in plasma or serum, significant loss of label could occur when the labeled liposomes were introduced into an animal.

Despite attempts to develop stable $^{99m}$Tc-labeled liposomes, there has been little success. In a thoroughly detailed review of liposomal labeling with radioactive technetium, Barratt et al. noted that technetium labeling techniques vary widely in efficiency. Moreover, stability is generally recognized to be poor, especially in vivo. Most methods of labeling liposomes with $^{99m}$Tc encapsulate the $^{99m}$Tc during liposome manufacture. However, these encapsulation methods do not solve the problem of in vivo dissociation of $^{99m}$Tc from the liposome. The dissociated $^{99m}$Tc is usually visualized in the kidneys and bladder. These problems clearly illustrate that development of a reliable method to load high levels of $^{99m}$Tc into liposomes without in vivo dissociation would be beneficial in view of the many clinical uses for radiolabeled liposomes (Hwang, K. J. in Liposomes from Biophysics to Therapeutics, M. J. Ostro, Ed., Marcel Dekker, New York, 1987).

There are numerous clinical applications for $^{99m}$Tc-liposomes. Comparison studies of liposome scanning, bone scanning and radiography have been performed in inflammatory joint disease. Liposome scans have been shown to be positive only in clinically active inflammatory disease. The method has also been able to discriminate between different grades of joint tenderness, in contrast to bone scans (O'Sullivan, M. M., Powell, N., French, A. P., Williams, K. E., Morgan, J. R., and Williams, B. D., *Ann. Rheum. Dis.* 47, 485–491, 1988; Williams, B. D., O'Sullivan, M. M., Saggu, G. S., et al., Ann. Rheum. Dis. (UK), 46, 314–318 (1987)). Other studies include the localization of abscesses (Morgan, J. R., Williams, K. E., Davies, R. L., et al., *J. Med. Microbiol.* 14, 213–217 (1981); tumor scanning (Eisenhut, M., *Therapiewoche* (West Germany) 30, 3319–3325 (1980); lymph node imaging (Osborne, M. P., Richardson, V. J., Jeyasingh, K., Ryman, B. E., *Int. J. Nucl. Med. Biol. (England)* 6, 75–83 (1979; Yu, B., Chin. *J. Oncol.* (China) 10, 270–273 (1988); clearance in the human lung (Farr, S. J., Kellaway, I. W., Parry-Jones, D. R., Woolfrey, S. G., *Int. J. Pharm.* (Netherlands) 26, 303–316 (1985)); and infarction (Palmer, T. N. Caride, V. J., Caldecourt, M. A., Twickler, J., and Abdullah, V., *Biochim. Biophys. Acta* 797, 363–368 (1984)).

Other potential uses of a liposome label include cardiac gated blood pool angiography and gastrointestinal bleeding detection. The most commonly used process known as the modified in vivo technique is fairly lengthy and requires 2-3 injections into the patient. For red blood cell labeling, the patient is injected with 1-2 mg of stannous PYP (Callahan, R. J., et al., *J. Nuclear Medicine* 23, 315–318 (1982)). Fifteen minutes later a blood sample is withdrawn and incubated with $^{99m}$TcO$_4^-$ (free pertechnetate). The patient is then reinjected with the radiolabeled blood, the whole procedure requiring up to 1 hour. The major disadvantage of this technique is that the label is often poor and free pertechnetate is taken up in the stomach, resulting in intestinal contamination and making the results difficult to interpret. A rapid labeling technique would very likely alleviate this major problem, allowing improved cardiac and gastrointestinal bleeding detection imaging.

There is a distinct need for radiopharmaceutical materials that can be broadly applied to clinical applications and to biodistribution and bioimaging studies. $^{99m}$Tc labeled liposomes would appear to be an ideal reagent but present methods of labeling liposomes with $^{99m}$Tc are generally inefficient. A far greater problem is the lack of in vivo stability of $^{99m}$Tc labeled liposomes, thereby creating uncertainty in interpretation of results and limiting use.

The present invention provides clinicians with a highly stable $^{99m}$Tc label captured within a liposome. The labeled liposome encapsulated protein is useful in a wide range of clinical applications related to biodistribution and imaging.

SUMMARY OF THE INVENTION

A stable liposome-encapsulated protein labeled with $^{99m}$Tc and its novel method of preparation are the subject of the present invention. The method of preparation results in over 95% labeling efficiency and produces labeled liposomes that are surprisingly stable in vivo for relatively long periods of time.

The method utilizes liposome encapsulated protein. Most preferably this protein will be hemoglobin, although other proteins binding to selected labels could be chosen. Encapsulation of substances within liposomes is well-known and techniques for encapsulation have been described (Hwang, K. J. in Liposomes from Biophysics to Therapeutics, M. J. Ostro, Ed., Marcel Dekker, Inc., New York, 1987). In particular, a method for encapsulating hemoglobin in liposomes is described (U.S. Pat. No. 4,911,929, Farmer, M. C. and Beissinger, R. L., 1990). Hemoglobin is most preferred because it binds avidly with $^{99m}$Tc, presently the most widely used radionuclide in nuclear medicine (Barratt, G. M., Tuzel, N. S. and Ryman, B. E. in Liposome Technology, Vol. II, G. Gregoriadis, Ed., CRC Press, Boca Raton, 1984). Nevertheless, there may be instances in which other labels would be desired for specific studies or clinical purposes and thus a different protein would better serve to bind the label. Certain beta-emitters, for example, might be desired and such radionuclides might bind more tightly to albumin or to another protein. On the other hand, in certain applications, some disassociation of the label from the protein may be desirable, as in instances where the liposome is intended to deposit the label at target organs or body areas. The label would then be dispensed at the target area. In any event, it is contemplated that the protein encapsulated can be chosen with consideration of the desired effect.

In the incubation of a liposome encapsulated protein with a labeled carrier, the carrier must be capable of diffusing through the liposomal membrane and also complexing with the desired radionuclide. Generally this will require a carrier that is lipophilic and also sufficiently water soluble to permit efficient transfer within the water compartment of the lipid vesicle. For the radionuclide $^{99m}$Tc, the preferred carrier is hexamethylenepropylene amine oxime. This carrier transports the metal across the bilayer membrane of the liposome with subsequent transfer of the $^{99m}$Tc to the hemoglobin. It will be recognized that the preferred carrier will depend to some extent on the lipid composition and surface charge of the liposome which can be positive, negative or neutral. The preferred carrier, HMPAO, readily crosses the negatively charged membrane of the liposomes used in the practice of the invention. Other carriers would be chosen on their ability to complex with the selected radionuclide and the efficiency of transport across the liposomal membrane to mediate exchange with the encapsulated capture material.

Furthermore, special ligands on the liposome surface, oligosaccharides or immunoglobulins for example, could also affect uptake of the carrier as well as targeting of the liposomes within the body. The synthesis of liposomes with charged or neutral surfaces having a wide variety of compositions is well known in the art. The selection of the appropriate liposome would require some experimentation and would depend on the carrier chosen and in turn on the radionuclide required.

The carrier must be able to cross the liposomal membrane and must also bind with a radionuclide. The binding to the carrier should not be so tight that dissociation is insignificant. Two factors should be kept in mind. First, the carrier must bind tightly enough to a radionuclide to be able to efficiently transport the label into the liposome and second, the protein within the liposome must bind the label relatively tightly so that the label is retained within the liposome. In principle, it would probably not matter if the carrier were also bound to the capture material within the liposome, although it is preferred that the carrier after releasing the radionuclide is washed away so that less extraneous material is introduced during in vivo applications. Furthermore, carrier bound to the capture material would likely hinder efficiency of binding of the radionuclide to the encapsulated capture material.

The time required for the incubation of labeled carrier with liposome encapsulated protein will vary with the nature of the labeled carrier and the composition of the liposome. In a preferred embodiment, a $^{99m}$Tc-HMPAO complex is incubated 15-30 minutes with liposome encapsulated hemoglobin at room temperature. Once inside the liposome, the $^{99m}$Tc dissociates from the carrier and binds to hemoglobin. It appears that the $^{99m}$Tc binds to the β-chain of hemoglobin which is recognized as a strong binder of reduced $^{99m}$Tc (Dewanjee, M. K., J. Nucl. Med. 15, 703-706 (1974)). The inventors also contemplate that denatured or functionalized β-chain hemoglobin might bind well to a radionuclide.

Figure 7:
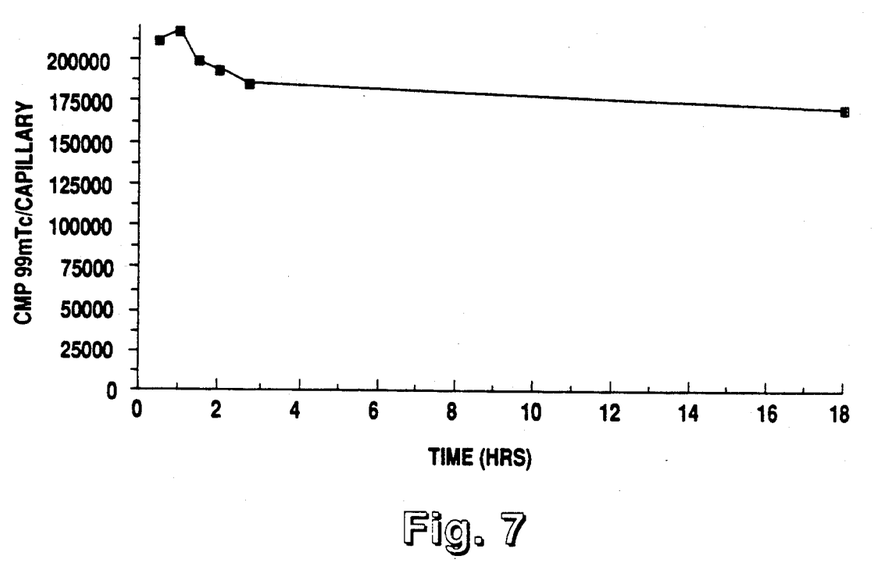
FIG. 7 is a graph of $^{99m}$Tc radioactive counts of capillaries drawn serially after infusion of 25 milliliters of $^{99m}$Tc-labeled LEH at a concentration of 50 mg total lipid per milliliter into a 2 kilogram New Zealand rabbit.

The labeling efficiency of this method is greater than 95% and stability in vivo is quite high, as indicated in the examples. After more than 18 hours, 70% of the injected liposome encapsulated $^{99m}$Tc labeled hemoglobin was recovered in vivo from rabbit blood (FIG. 7). No other method has reported this high stability in vivo. In fact, the present invention has overcome one of the most significant disadvantages in the use of $^{99m}$Tc as a radiolabeling agent, i.e., the apparent release of free technetium in vivo therefore casting doubt that the radioimages are representative of intact liposomes (Barratt, G. M., Tuzel, N. S. and Ryman, B. E. in Liposome Technology, Vol. II, G. Gregoriadis, Ed., CRC Press, Boca Raton, 1984)).

Another significant advantage of the present inventive method is the high labeling efficiency of encapsulated hemoglobin. There is consequently less need to separate $^{99m}$Tc from liposomes by time consuming techniques such as gel chromatography. When separation is desired, a simple centrifugation or syringe-pack column can be employed.

After incubation of $^{99m}$Tc-HMPAO with liposome encapsulated hemoglobin, excess labeled carrier may be washed from the liposome encapsulated labeled protein. Since the labeling is so efficient, only a few percent of the initial radioactivity is found in the wash and the major component is the unlabeled carrier. Since the preferred carrier, HMPAO, is nontoxic the washing is optional and the labeled liposomes may be used directly after incubation with $^{99m}$Tc-HMPAO If separation is desired, centrifugation at $10-20,000 \times g$ can be used or, a rapid and convenient separation could be effected with a syringe pack column attached to the syringe containing the labeled liposomes. The liposomes would be passed in the void volume while any free pertechnetate would be retained on the column. In a most preferred labeling procedure for clinical use, a freeze dried preparation of $^{99m}$Tc-HMPAO is reconstituted with $^{99m}$TcO$_4^-$ and immediately incubated at room temperature with liposome encapsulated hemoglobin for a period as short as 5 minutes prior to use in a patient. Washing is not necessary.

The role of the hemoglobin in binding 99mTc within the liposome is apparent when compared with labeling of empty liposomes. Blank liposomes lose over 90% of the label after a single wash. The present invention involves the discovery that the encapsulated protein, most preferably hemoglobin, within the liposome results in a highly stable $^{99m}$Tc label for the liposome.

The present invention also contemplates the use of $^{99m}$Tc labeled hemoglobin in kit form. Thus, in a preferred mode of use, freeze dried liposome encapsulated hemoglobin would be incubated with a radionuclide carrier, such as $^{99m}$Tc hexamethylenepropylene amine oxime, and used for administration to patients or experimental animals. Other radionuclides could be used as could other encapsulated proteins besides hemoglobin, for example albumin, as described in Example 2.

Example 3 illustrates the use of $^{99m}$Tc labeled liposome encapsulated hemoglobin in biodistribution studies, but it will be appreciated that appropriate carriers could be used to transfer other gamma emitters to capture agents within a liposome. For example, $^{111}$In, $^{125}$I and $^{67}$Ga. The method could also be applied to beta- or positron emitters; for example, $^{32}$P, $^{35}$S or, in the latter category, $^{68}$Ga and $^{18}$F. The distribution of the label can be detected by means appropriate to the emitter. Gamma emitters are commonly detected using well established scintillation counting methods or nuclear gamma cameras. Beta emitters can be detected by radiation detection devices specific for beta particles while positron emitters are determined using various designs of a positron emission tomography apparatus.

Likewise, the general method described in the present invention would be applicable to magnetic resonance imaging, simply by preparing a paramagnetically labeled liposome encapsulated carrier molecule, for example hemoglobin, administering the labeled liposome in vivo and determining the distribution of the paramagnetic labeled hemoglobin. The usual means for determining paramagnetic species is nuclear magnetic resonance detection.

In another aspect of the invention, $^{99m}$Tc labeled LEH is used to label neutrophils. The 20% labeling achieved was surprisingly high compared with efforts by others to label these cells.

DETAILED DESCRIPTION OF THE PREFERRED EMBODIMENTS

Liposome Encapsulated Protein

As discussed above, several different proteins as well as different liposomal compositions can be used. Albumin is an example of a protein that can be encapsulated by the method described in Example 1 used to encapsulate hemoglobin. In a most preferred embodiment, hemoglobin is encapsulated in monolamellar negatively charged liposomes. Methods of producing liposome encapsulated protein include a variety of methods, for example, reverse phase evaporation, homogenization and pressure extrusion. A method of producing liposome encapsulated hemoglobin is described in Example 1. Other forms of hemoglobin can be substituted for bovine hemoglobin, including recombinant human hemoglobin. Well-known methods of encapsulation with liposomes could be employed to encapsulate proteins with special affinity for a desired label. The encapsulated protein need not be a native molecule or even the entire molecule. For example, only the $\beta$-chain of hemoglobin would be required to bind $^{99m}$Tc. Examples of other proteins that could be encapsulated include transferrin, myoglobin, myosin, ferritin, globulin, insulin, elastin, keratin, casein, hemoglobin fragments and other polypeptides that bind to $^{99m}$Tc.

$^{99m}$Tc Carriers

The $^{99m}$Tc carrier found most appropriate is an alkylenepropyleneamine oxime that complexes with the $^{99m}$Tc and can be purchased as a lyophilized preparation (Cereteo TM, Amersham, Ill.). In this form, the HMPAO is mixed with sterile eluate from a technetium Tc-$^{99m}$ generator. The generator eluate may be adjusted to a radioactive concentration of between 0.37–1.11 GBq (10–30 mCi) in 5 ml by dilution with preservative-free, non-bacteriostatic saline prior to mixing with 0.5 mg of HMPAO. The $^{99m}$Tc complex forms almost immediately and is then incubated with liposome encapsulated hemoglobin at room temperature for 5–15 minutes. Room temperature incubation is a significant advantage over other methods of liposome labeling presently used. $^{111}$In, for example, can be retained within liposome encapsulated nitrilotriacetic acid but the encapsulated nitrilotriacetic acid must be incubated with $^{111}$indium chloride at 60° C. for 30 minutes. Thus $^{99m}$Tc labeled liposomes prepared by the method of the present invention could be used in the assessment of in vivo distribution of new liposome drug agents that contain proteins or other heat labile drugs, whereas the heat required for the preparation of the $^{111}$In labeled liposome would denature or destroy any encapsulated heat sensitive material.

$^{99m}$Tc liposomes also have potential in assessing the effectiveness of targeting with liposomes having antibodies attached to the surface. Antibodies to infectious agents or to tumor cells would bind to the targeted areas allowing radioimaging and possible delivery of drugs to the site.

EXAMPLE 1

Preparation of Liposome Encapsulated Hemoglobin

The components of LEH vesicles are: lipid soybean phosphatidylcholine (soyPC) (American Lecithin Company, Atlanta, Ga.), supplied as Phospholipon 100-H composed of 95% hydrogenated distearoyl phosphatidylcholine and up to 5% lysophosphatidylcholine; cholesterol (Calbiochem, San Diego, Calif.) at a purity of greater than 99% by TLC; and Dimyristoyl phosphatidyl DL-glycerol (DMPG) (Avanti Polar Lipids, Birmingham, Ala.) which was used without further purification. d-Alpha-tocopherol (Sigma, St. Louis, Mo.) was mixed in a 200 mg/ml solution in chloroform. All lipids were dried down from chloroform stock solutions in a mole ratio of 10:9:1 (soy pC:cholesterol:DMPG:alpha-tocopherol) and stored overnight in a vacuum desiccator to remove organic solvent. Samples were then rehydrated with solutions of trehalose (Pfanstiehl Laboratories. Waukegan, Ill.) in 30 mM phosphate buffered saline pH 7.4 and warmed in a water bath at 60° C. for one hour.

The resultant multilamellar vesicles formed from rehydration were reduced to large unilamellar vesicles (LUVs) using a high shear, high pressure apparatus (Microfluidics Corp., Boston, Mass.). The LUV's were then frozen in liquid nitrogen and lyophilized. The resultant dry sugar-lipid preparations were then hydrated with a solution of concentrated (25g/ml) bovine hemoglobin (Hb) (Biopure Corp., Boston, Mass.) and placed on an orbital shaker at 4° C. for 2 hours. These solutions were then run through the microfluidizer to form LEH and centrifuged to remove extravesicular hemoglobin (14,000×g for 1 hour). The resulting LEH was concentrated by centrifugation and stored in the refrigerator at 4° C. or shell frozen using a bench top lyophilizer.

EXAMPLE 2

$^{99m}$Tc Labeling of Liposome Encapsulated Hemoglobin

Liposome encapsulated hemoglobin (prepared as described or purchased from Vestar, Inc., San Dimas, Calif. or Naval Research Laboratories, Washington, D.C.) was washed 3 times with phosphate buffered saline by centrifugation and resuspended with phosphate buffered saline to remove subcellular-sized debris and free hemoglobin. LEH was resuspended in PBS to yield a hematocrit value of approximately 50. $^{99m}$Tc (10 mCi) in 5 ml sterile water for injection was used to reconstitute hexamethylenepropylene amine oxime (HMPAO) supplied as a freeze dried preparation (Ceretec TM, Amersham, Arlington Heights, Ill.) for 5 min at room temperature. The $^{99m}$Tc-HMPAO complex was then incubated with LEH (10 mg-1000 mg total lipid dose of LEH containing 2.5-300 mg intravesicular hemoglobin) for 5 minutes with intermittent swirling after which the radio-labeled LEH was washed (centrifugation at 20,000×g for 30 minutes) with PBS and the labeling efficiency determined (bound to pellet/total). LEH was then resuspended to a constant lipid dose for injection.

Figure 1:
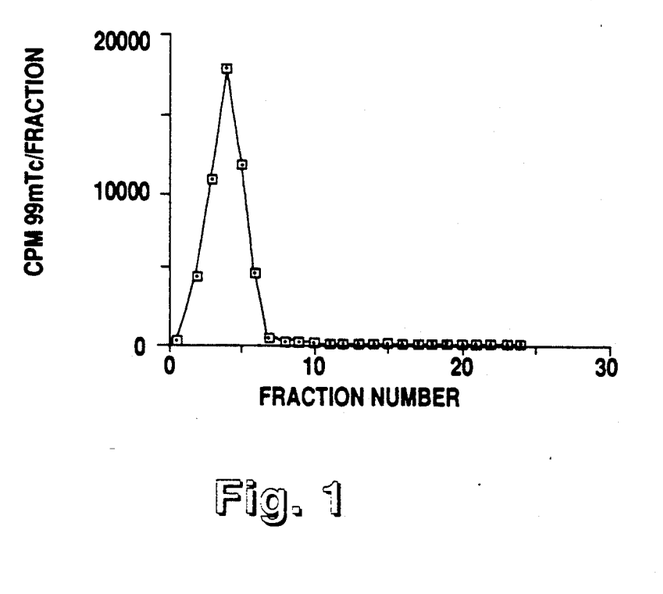
FIG. 1 is a graph showing the fractionation of liposome encapsulated $^{99m}$Tc labeled liposomes on a Sephadex G-200 column 70 hours after binding of the label to the encapsulated hemoglobin. All the $^{99m}$Tc is associated with the liposomal fraction.
Figure 2:
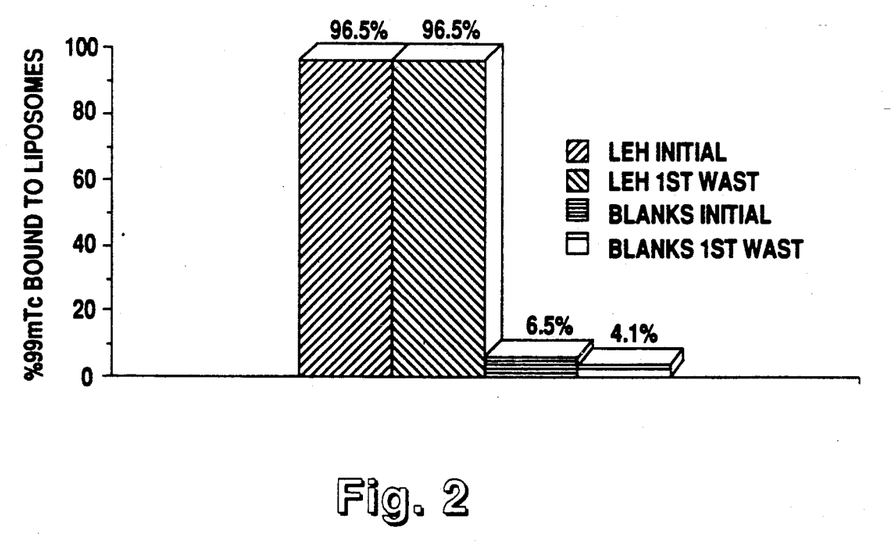
FIG. 2 shows the percent $^{99m}$Tc binding initially to liposomes using HMPAO where LEH is liposome encapsulated hemoglobin and blanks are liposomes without encapsulated material. There is no loss of the $^{99m}$Tc label during the first wash.

Fractionation of $^{99m}$Tc-labeled LEH on Sephadex G-200 70 hours after binding is shown in FIG. 1. The labeled LEH eluted with the void volume. There was insignificant detection of free $^{99m}$Tc. FIG. 2 indicates that liposomes without hemoglobin (blanks) bound less than 10% of the $^{99m}$Tc added to LEH preparations. The blanks were prepared as described in Example 1 for the preparation of LEH except that during hydration no bovine hemoglobin was added.

Figure 3:
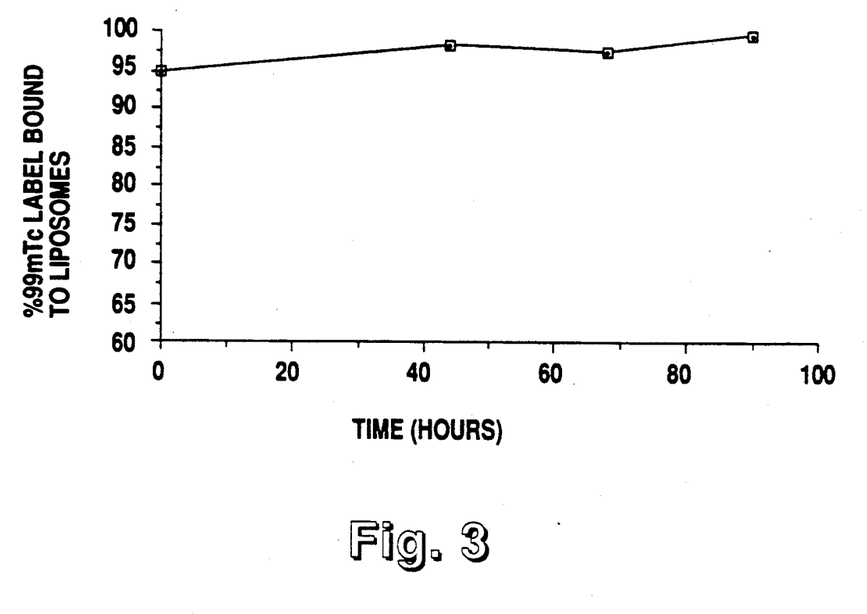
FIG. 3 shows the in vitro stability of $^{99m}$Tc labeled liposomes in lactated Ringers solution at 2° C.

The $^{99m}$Tc-labeled LEH exhibited excellent in vitro stability over a period of at least 90 hours storage in lactated Ringer's solution, as shown in FIG. 3.

Figure 4:
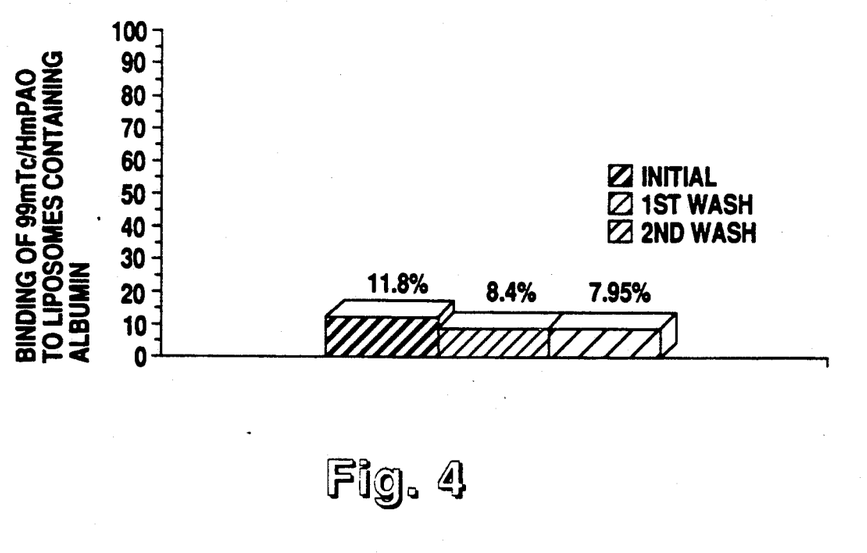
FIG. 4 shows 11.8% initial binding of $^{99m}$Tc to liposome encapsulated albumin.

Liposome encapsulated albumin was prepared as described for hemoglobin. Approximately 12% of the label carried by the $^{99m}$TcHMPAO became bound to the encapsulated albumin. One-third of the label was removed after two washings with PBS (see FIG. 4).

EXAMPLE 3

Animal Biodistribution Studies with $^{99m}$Tc-labeled LEH

Figure 5A:
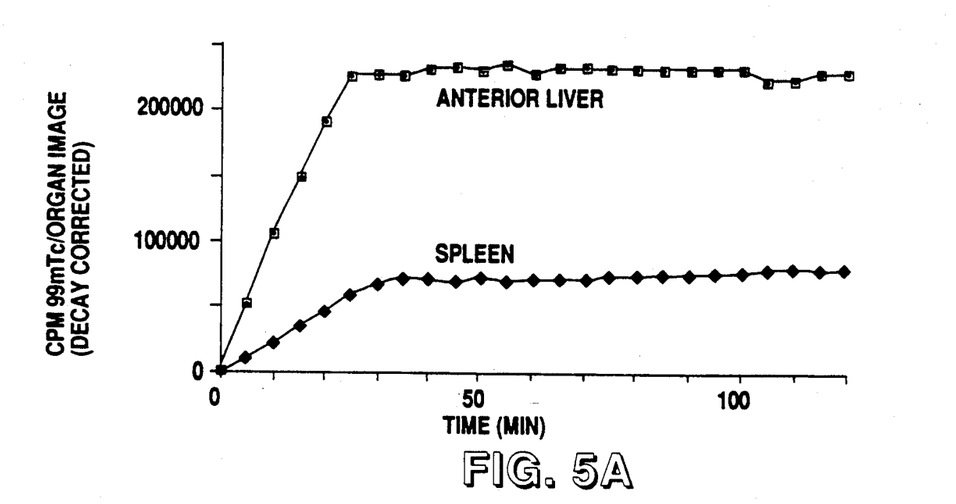
FIGS. 5(A), 5(B) and 5(C) show time activity curves acquired from imaging data of the heart, liver, spleen, bladder and lung of a rabbit injected with $^{99m}$Tc labeled LEH.
Figure 5B:
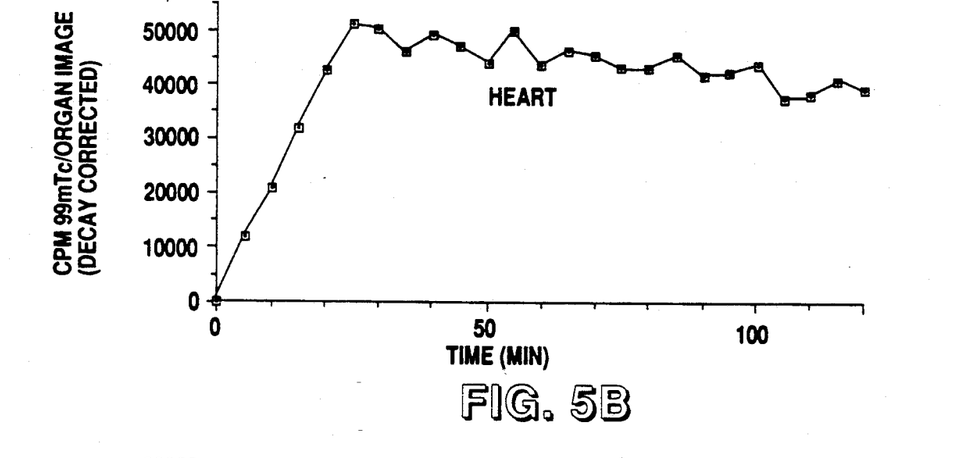
Figure 5C:
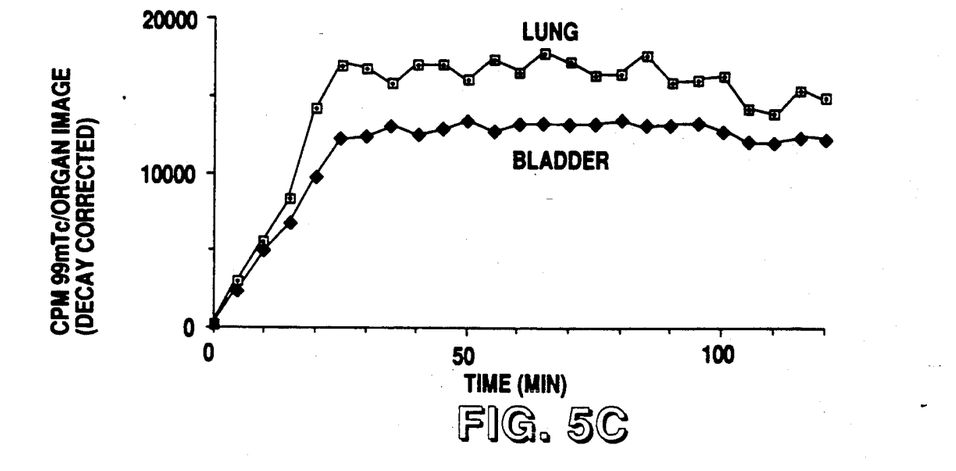
Figure 6:
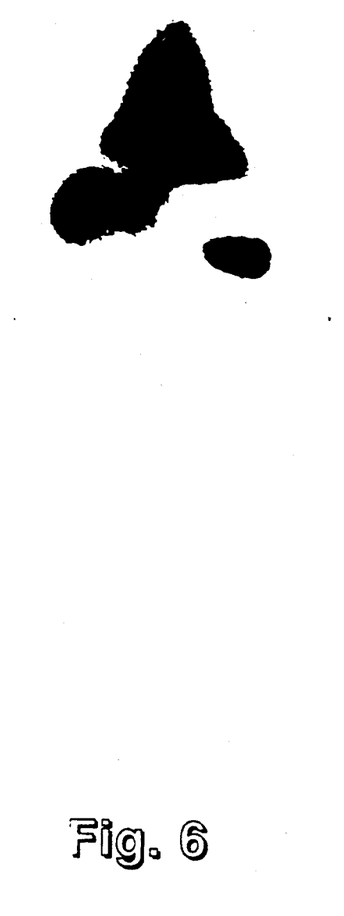
FIG. 6 shows various anatomical features seen on the image of a New Zealand rabbit infused with $^{99m}$Tc-labeled LEH acquired at 2 hours labeling.

Young adult male New Zealand white rabbits (2.5-3.0 kg) were anesthetized intramuscularly with ketamine:xylazine at 50 mg/kg:10mg/kg respectively. While anesthetized, venous and arterial access lines were secured. The rabbit was then restrained in the supine position under a low energy, parallel hole collimator of a gamma camera and imaged for $^{99m}$Tc activity at 140 Kev with a 20% window. Baseline blood samples were drawn and the metered (40 ml/kg/hr) injection of the LEH was begun. An aliquot of the injection material was reserved for lipid analysis and radioactive quantitation. Blood was then drawn at intervals to assess changes in blood chemistry, complete blood counts, the duration of LEH in the circulation and subsequent deposition and processing of the LEH by the organ systems. At 20 hours postinjection, the rabbit was sacrificed by anesthesia overdose and tissues recovered for quantitation and pathology study. Images acquired for the first two hours and at 20 hours were analyzed by drawing regions of interest around all organ systems (heart, lungs, anterior and posterior liver, spleen, kidneys, bladder and aorta) within the camera field of view. Counts in these regions of interest were calculated at 1 min intervals for 2 hours and then at 20 hours. Counts were decay corrected to correct for radioactive decay. These data were entered into a MacIntosh computer for graphic demonstration of changes in biodistribution occurring with time as shown in FIG. 5. The levels of $^{99m}$Tc distribution in the rabbit heart, liver, spleen and lungs are shown in FIG. 6.

The in vivo recovery of $^{99m}$Tc-labeled LEH from rabbit blood over a period of 18 hours is shown in FIG. 7.

EXAMPLE 4

$^{99m}$Tc-Labeling of Neutrophils

Figure 8:
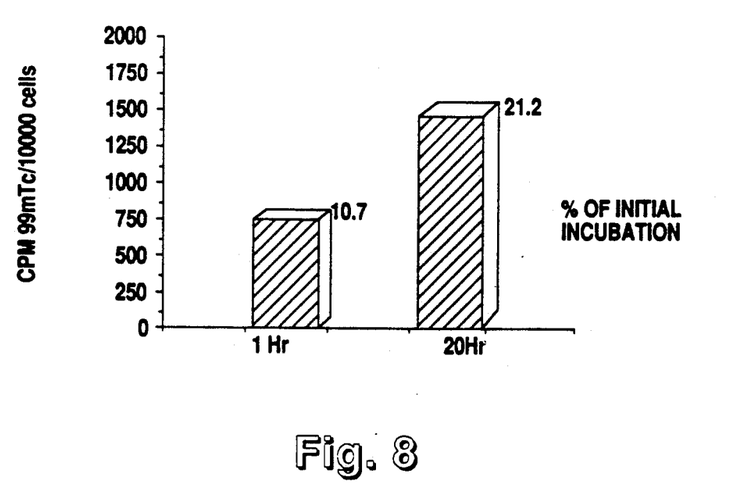
FIG. 8 shows the labeling of neutrophils incubated with $^{99m}$Tc labeled liposome encapsulated hemoglobin. The radioactivity remaining after washing of the neutrophils is 10.7% after 1 hour of incubation and 21.2% after 20 hours of incubation.

Sixty ml of whole blood was drawn and diluted with 3 volumes of Hanks Buffered Salt Solution. Neutrophils were isolated with Ficol Hypaque centrifugation at 600×g for 20 minutes. Recovered neutrophils were washed ×2 with a lymphocyte maintenance medium. The neutrophils were counted and 2 separate aliquots of $10^7$ neutrophils were incubated with radiolabeled LEH for 1-20 hours at 37° C. The suspensions were counted and then centrifuged to yield a neutrophil pellet. The pellet was resuspended and washed ×2. The labeling efficiency was then determined (bound to white cell pellet/total). As shown in FIG. 8, over 20% of the initial activity was incorporated by the neutrophils after 20 hours of incubation.

The present invention has been described in terms of particular embodiments found by the inventors to comprise preferred modes of practice of the invention. It will be appreciated by those of skill in the art that in light of the present disclosure numerous modifications and changes can be made in the particular embodiments exemplified without departing from the intended scope of the invention. For example, other proteins or protein fragments could replace hemoglobin as the encapsulated capture agent for a radionuclide without affecting the intended nature and practice of the invention. All such modifications are intended to be included within the scope of the claims.

The references listed below are incorporated herein by reference to the extent that they supplement, explain, provide a background for or teach methodology, techniques and/or compositions employed herein.

What is claimed is:

1. A method of preparing stable gamma-emitting radionuclide-labeled alkyleneamine oxime, said incubating being for a period of time sufficient to form labeled liposome-encapsulated protein.

2. The method of claim 1 wherein excess gamma-emitting radionuclide-labeled alkylene amine oxime is washed from the labeled liposome-encapsulated protein.

3. The method of claim 1 wherein the labeled lipsome-encapsulated protein is hemoglobin.

4. The method of claim 1 wherein the liposome-encapsulated protein is a $^{99m}$Tc-binding protein selected from the group consisting of albumin, transferrin, myoglobin, myosin, insulin, globulin, casein, keratin, lectin, ferritin and elastin.

5. The method of claim 2 wherein the protein is at least partially denatured.

6. The method of claim 1 wherein the protein is the β-chain of hemoglobin.

7. The method of claim 1 wherein the gamma-emitting radionuclide is, $^{51}$Cr, $^{59}$Fe, $^{67}$Ga, $^{86}$Rb, $^{99m}$Tc, or $^{111}$In.

8. The method of claim 1 wherein the gamma-emitting radionuclide-labeled alkylene amine oxime is $^{99m}$Tc-hexamethylenepropylene amine oxime.

9. The method of claim 1 wherein the labeled liposome-encapsulated protein is $^{99m}$Tc-labeled liposome encapsulated hemoglobin.

10. The method of claim 1 wherein the charge on the liposome is negative.

11. A kit useful for preparing liposome encapsulated radiolabeled protein comprising:
   a transporter being compartmentalized to receive one or more container means in close confinement therein;
   a first container means comprising an alkyleneamine oxime being capable of binding to a radionuclide; and
   a second container means comprising liposome encapsulated protein, said protein having greater affinity for radionuclide than the affinity of alkyleneamine oxime for said protein, and said liposome being permeable to said alkyleneamine oxime.

12. The kit of claim 11 wherein the carrier and the liposome encapsulated protein are each lyophilized.

13. The kit of claim 11 wherein the carrier is hexamethylenepropyleneamine oxime or propyleneamine oxime.

14. The kit of claim 11 wherein the radionuclide is $^{99m}$Tc, $^{67}$Ga or $^{111}$In.

15. The kit of claim 11 wherein the protein is hemoglobin, albumin, myoglobin, transferring or ferritin.

* * * * *

UNITED STATES PATENT AND TRADEMARK OFFICE
CERTIFICATE OF CORRECTION

PATENT NO. : 5,158,760
DATED : October 27, 1992
INVENTOR(S) : William T. Phillips, et al It is certified that error appears in the above-indentified patent and that said Letters Patent is hereby corrected as shown below:

In claim 1 at column 11, line 7, insert after the word "stable" and before the word "gamma-emitting" --radiolabeled liposomes, comprising incubating liposome-encapsulated protein with a--.

In claim 3 at column 11, lines 16-17, change "lipsome" to --liposome--.

In claim 5 at column 11, line 24, change claim "2" to claim --1--.

In claim 15 at column 12, line 30, change "transferring" to --transferrin--.

Signed and Sealed this

Fifth Day of October, 1993

Attest:

BRUCE LEHMAN

*Attesting Officer*   Commissioner of Patents and Trademarks